US010351505B2

(12) United States Patent
Souvaliotis et al.

(10) Patent No.: US 10,351,505 B2
(45) Date of Patent: Jul. 16, 2019

(54) INTEGRATED PROCESS FOR THE PRODUCTION OF PARTIAL OXIDATION PRODUCT DERIVATIVES

(71) Applicant: ExxonMobil Chemical Patents Inc., Baytown, TX (US)

(72) Inventors: Athanassios Souvaliotis, Houston, TX (US); Caiguo Gong, Houston, TX (US); Moses O. Jejelowo, Missouri City, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 293 days.

(21) Appl. No.: 15/527,487

(22) PCT Filed: Nov. 3, 2015

(86) PCT No.: PCT/US2015/058747
§ 371 (c)(1),
(2) Date: May 17, 2017

(87) PCT Pub. No.: WO2016/099676
PCT Pub. Date: Jun. 23, 2016

(65) Prior Publication Data
US 2018/0334422 A1 Nov. 22, 2018

Related U.S. Application Data

(60) Provisional application No. 62/092,612, filed on Dec. 16, 2014.

(30) Foreign Application Priority Data

Mar. 3, 2015 (EP) .................................. 15157266

(51) Int. Cl.
*C07C 67/04* (2006.01)
*C07C 27/14* (2006.01)
*C07C 69/01* (2006.01)

(52) U.S. Cl.
CPC .............. *C07C 67/04* (2013.01); *C07C 27/14* (2013.01); *C07C 69/01* (2013.01)

(58) Field of Classification Search
CPC ......... C07C 67/04; C07C 69/01; C07C 27/14; C07C 69/06; C07C 11/24; C07C 69/15
See application file for complete search history.

(56) References Cited

U.S. PATENT DOCUMENTS

2002/0099239 A1  7/2002  Ellis et al.
2005/0049434 A1  3/2005  Tustin et al.
(Continued)

FOREIGN PATENT DOCUMENTS

CN    1 311 181 A    9/2001
RU    2 208 600 C    7/2003

Primary Examiner — Jafar F Parsa
(74) Attorney, Agent, or Firm — Kevin M. Faulkner

(57) ABSTRACT

An integrated process for the production of one or more acetylene derivatives is provided. The integrated process includes a) partially oxidizing a hydrocarbon feedstock to produce a partial oxidation mixture comprising $H_2$, CO, and acetylene, b) providing the $H_2$ and CO of the partial oxidation mixture to a collocated methanol production process to produce a methanol-containing effluent; c) providing the methanol-containing effluent to a collocated carbonylation process to produce an acetic acid-containing effluent; and d) providing the acetylene of the partial oxidation mixture and the acetic acid-containing effluent to one or more of the collocated acetylene-derivative processes following: i) a vinyl acetate monomer production process; ii) an oxidation unit for the production of formaldehyde from the methanol-containing effluent; iii) a vinyl chloride monomer production process, and/or iv) a 1,4-butanediol production process.

20 Claims, 8 Drawing Sheets

(56) References Cited

U.S. PATENT DOCUMENTS

2006/0281942 A1   12/2006   Ferguson et al.
2010/0234476 A1   9/2010   Lin et al.
2014/0058127 A1   2/2014   Bricker et al.
2014/0058138 A1   2/2014   Bricker et al.

INTEGRATED PROCESS FOR THE PRODUCTION OF PARTIAL OXIDATION PRODUCT DERIVATIVES

CROSS REFERENCE TO RELATED APPLICATION

This application is a National Stage Application of International Application No. PCT/US2015/058747, filed Nov. 3, 2015, and claims priority to and the benefit of U.S. Ser. No. 62/092,612, filed Dec. 16, 2014, and EP application 15157266.6, filed Mar. 3, 2015, the disclosures of which are incorporated herein by reference in their entireties.

FIELD OF THE INVENTION

The invention relates to integrated processes for the production of one or more derivatives from the partial oxidation of a hydrocarbon feedstock, e.g., natural gas. In particular embodiments, the processes relate to the production of such derivatives having a lower concentration of one or more contaminants and/or an improved carbon footprint.

BACKGROUND OF THE INVENTION

Gasification has long been used to convert hydrocarbons, e.g., coal and/or coke, to higher value products. Historically, large amounts of acetylene are produced in this manner, particularly where coal deposits are plentiful. While gasification may be commercially viable, it is widely acknowledged that coal gasification by-products are difficult to handle.

As an alternative, steam cracking reactors are commonly utilized to convert the hydrocarbon feed into ethylene and acetylene, which may be further processed into various chemical products. Under the relatively high severity conditions used to produce appreciable amounts of acetylene, coke formation can occur.

Due to its reactive nature, acetylene is usually produced in small quantities and used proximate to its production facility. Thus, some other reactants for the production of compounds derived from acetylene are typically transported, for example by railroad or ship, to the location where the acetylene is manufactured, thereby adding cost and increasing the carbon impact of the overall process. In many cases, the added time and environmental conditions associated with transport or such reagents requires the use of unwanted stabilizers and impurities that can inhibit or contaminate downstream reactions and/or products.

Thus, there remains a need for integrated processes that convert a feedstock to acetylene and various other reactants useful for making acetylene derivatives. There is also a need for such a process that reduces or eliminates the need for stabilizers and/or impurities in one or more reactants for making acetylene derivatives and/or reduces the carbon impact of one or more such processes.

SUMMARY OF THE INVENTION

The invention relates, in part, to the realization that the quality of one or more derivatives of acetylene may be improved by the integrated production of acetylene and other reactants used in the manufacture of such acetylene-based derivatives, e.g., vinyl acetate monomer, vinyl chloride monomer, acrylic acid, and/or 1,4-butanediol, from natural gas compositions, particularly gas sources rich in methane. The invention relates, in part, to the discovery of processes of such derivatives, wherein the processes can be collocated, thereby reducing the carbon impact of the manufacturing process.

Thus, in one aspect, the invention relates to an integrated process for the production of one or more acetylene derivatives, the process comprising: a) partially oxidizing a hydrocarbon feedstock comprising 10 wt % or more of one or more $C_1$-$C_4$ alkanes to produce a partial oxidation mixture comprising hydrogen, CO, and acetylene; b) providing at least a portion of the hydrogen and CO of the partial oxidation mixture to a collocated methanol production process to produce a methanol-containing effluent; c) providing at least a portion of the methanol-containing effluent to a collocated carbonylation process to produce an acetic acid-containing effluent; and d) providing at least a portion of the acetylene of the partial oxidation mixture and at least a portion of the acetic acid-containing effluent to one or more collocated acetylene-derivative processes following: i) a vinyl acetate monomer production process; ii) an oxidation unit for the production of formaldehyde from the methanol-containing effluent; iii) a vinyl chloride monomer production process, and/or iv) a 1,4-butanediol production process.

DETAILED DESCRIPTION OF THE INVENTION

Definitions

For the purposes of this invention and the claims thereto, the new numbering scheme for the Periodic Table Groups is used as described in Chemical and Engineering News, 63(5), pg. 27, (1985).

As used herein the term "integrated" means that the recited process steps are collocated.

As used herein the term "collocated" refers to one or more reactant production processes and a product production process. Reactant and product production processes are collocated when the production of each primary reactant process is in fluid communication with an inlet of the product production process. The phase "in fluid communication with" does not include processes where a primary reactant is transported via truck, rail or ship, to a product production process inlet.

The phase "primary reactant" may differ depending on the product production process. For example, the "primary reactants" of the partial oxidation process described herein include the hydrocarbon feedstock. The primary reactants of the methanol production process include syngas, i.e., a mixture of hydrogen and carbon monoxide. The "primary reactants" of the carbonylation process comprise carbon monoxide and methanol. The "primary reactants" of a vinyl acetate monomer (VAM) production process comprise acetylene and acetic acid. The "primary reactants" of an oxidation unit comprise methanol. The "primary reactants" of a diol unit comprise formaldehyde and acetylene. The "primary reactants" of a vinyl chloride monomer (VCM) unit comprise hydrogen chloride and acetylene.

As used herein the phase "comparable process" refers to a process where one or more of the component processes are not collocated.

The Integrated Process

Figure 1:
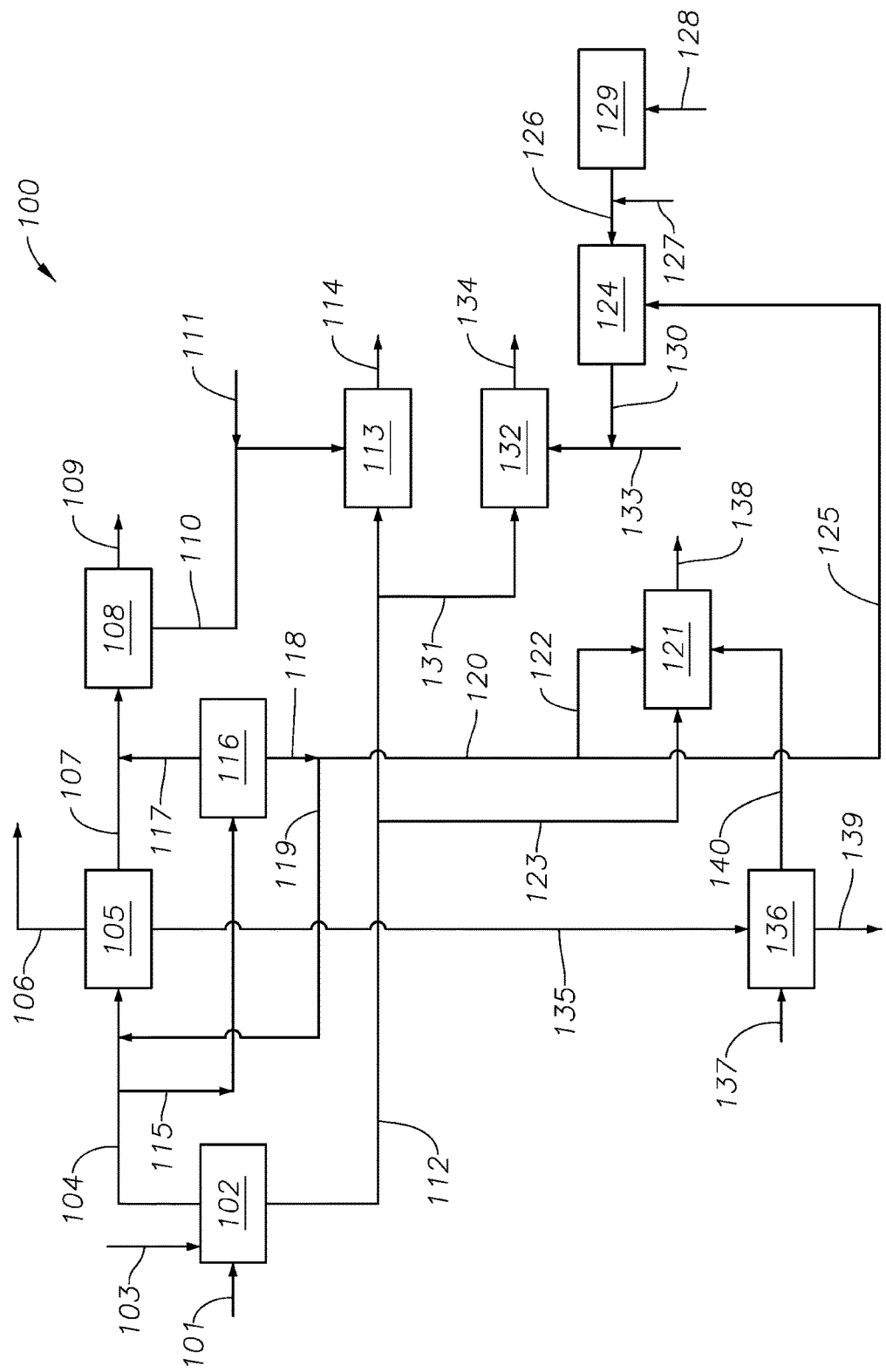
FIG. 1 illustrates an embodiment of the integrated process according to the invention.

FIG. 1 schematically illustrates an integrated process 100 for the production of one or more acetylene derivatives. In process 100 a hydrocarbon feedstock 101 is provided to partial oxidation process 102 along with an oxygen-containing gas, typically air via e.g., conduit 103. The hydrocarbon feedstock 102 may comprise about 10.0 to about 100.0 wt %, e.g., about 20.0 to about 100.0 wt %, about 30.0 to about 100.0 wt %, about 40.0 to about 100.0 wt %, about 50.0 to about 100.0 wt %, about 60.0 to about 100.0 wt %, about 70.0 to about 100.0 wt %, about 80.0 to about 100.0 wt %, about 90.0 to about 100.0 wt %, about 95.0 to about 100.0 wt %, about 99.0 to about 100.0 wt % of one or more $C_1$-$C_4$ alkanes, e.g., methane, ethane, propane, and butane and mixtures and isomers thereof, particularly methane, particularly methane, e.g., >80.0 wt % methane or >about 85.0 wt % methane. Partial oxidation process 102 converts at least a portion of the feedstock to a partial oxidation mixture comprising hydrogen, CO, and acetylene.

Hydrogen and CO produced in partial oxidation process 102 are removed from the process 102 by one or more conduits 104 and provided to other processes. For example, at least a portion of the hydrogen and CO may be provided to methanol production process 105. Optionally, at least a portion of methanol produced in methanol production process 105 may be removed from the integrated process 100 via e.g., one or more conduits 106. Additionally or alternatively, at least a portion of the methanol produced in methanol production process 105 may be combined with a CO source and provided, e.g., via conduit 107, to carbonylation process 108 for conversion to acetic acid, which may optionally be removed from the process 100 via e.g., conduit 109. Additionally or alternatively, at least a portion of the acetic acid produced by the carbonylation process 108 may be combined, e.g., via conduit 110 with an oxygen containing gas, e.g., air, via conduit 111 and acetylene, e.g., acetylene from partial oxidation process 102 via, e.g., conduit 112 for conversion into vinyl acetate monomer (VAM) in VAM production unit 113. Vinyl acetate monomer so produced may be removed from the process 100 via, e.g., conduit 114 for further processing according to any suitable process.

Additionally or alternatively, at least a portion of the hydrogen and the CO from process 102 may be provided via one or more conduits 115 to a hydrogen/CO separation process 116. At least a portion of the CO separated in process 116 may be provided to the carbonylation process 108 via, e.g., one or more conduits 117. Hydrogen exits the separation process 116 via outlet conduit 118. At least a portion of the hydrogen in outlet conduit 118 may be directed to methanol conversion process 105, e.g., via one or more conduits 119. Additionally or alternatively, at least a portion of the hydrogen exiting process 116 via outlet conduit 118 may be directed via, e.g., one or more conduits 120 for further use in process 100. For example, at least a portion of the hydrogen in conduits 120 may be provided to diol unit 121 via conduit 122 along with acetylene, e.g., from partial oxidation process 102 via conduit 123. Diol, e.g., 1,4-butanediol, exits the process 100 via conduit 138.

In some embodiments, at least a portion of the hydrogen from process 116 may be directed to hydrogen chloride unit 124, e.g., via conduit 125. A chlorinating agent, e.g., chlorine, is provided, e.g., via conduit 126 to hydrogen chloride unit 124 along with the hydrogen from conduit 125. The chlorinating agent may be provided from any convenient source, chlorine gas, via conduit 127 and/or as the effluent from a chlorine production unit, e.g., the electrochemical separation of chlorine from a brine source 128 in chlorine production unit 129. Alternatively, HCl may be obtained by cracking of ethylene dichloride. Effluent 130 from hydrogen chloride unit 124 may be combined with acetylene from partial oxidation process 102, e.g., via conduit 131 to form vinyl chloride monomer (VCM) in VCM unit 132. Additionally or alternatively, hydrogen chloride may be provided to VCM unit 132 via conduit 133. VCM, so produced, may be removed from the process 100 for further processing, storage, and/or transport via, e.g., conduit 134.

In some embodiments, at least a portion of the methanol from methanol production process 105 may be provided, e.g., via conduit 135, to oxidation unit 136 where it is combined with an oxygen-containing gas, e.g., air via conduit 137. Oxidation unit 136, typically converts at least a portion of the methanol to formaldehyde, at least a portion of which may be provided to diol unit 121, via e.g., conduit 138. Additionally or alternatively, the effluent from oxidation unit 136 may be removed from the process or recycled via effluent stream 139.

Partial Oxidation Process 102

The partial oxidation process 102 may be any process for converting a feedstock to a mixture comprising $H_2$, CO, and acetylene. One such method is high-temperature partial oxidation. Depending on the method used to supply the necessary endothermic heat of pyrolysis, the methane and/or hydrocarbon pyrolysis to acetylene process is broadly categorized into one-step and two-step processes. As a whole, the partial oxidation reactor system includes three major parts: the top one is a mixing zone with a diffuser, the second part (underneath) is a water-jacketed burner immediately followed by a reaction zone, and the final part is a quenching zone using water or heavy oil as a coolant. A perforated plate is typically used to cover the burner for control purposes. The ratio of acetylene to synthesis gas in the product stream can be controlled and optimized by controlling the ratio of the feedstock to oxygen-containing.

A two-stage high temperature pyrolysis (HTP) process may also be used. Typically, such two-stage processes include two main reaction zones followed by a quenching zone. The first reaction zone serves as a stoichiometric combustor to supply the necessary endothermic heat of hydrocarbon pyrolysis taking place in the second reaction zone, into which a fresh hydrocarbon feed such as methane is introduced. In the quenching zone, water or heavy oil is used as a coolant to cool down instantaneously the hot product gas from the pyrolysis zone. Similarly, a certain quantity of carbon will be formed in this two-step pyrolysis process. The acetylene concentration produced in the two step pyrolysis method is about double the acetylene produced in the one stage partial oxidation process. The amount of acetylene produced can also be increased by injection of methanol into the reaction zone during thermal cracking of hydrocarbons.

Figure 2:
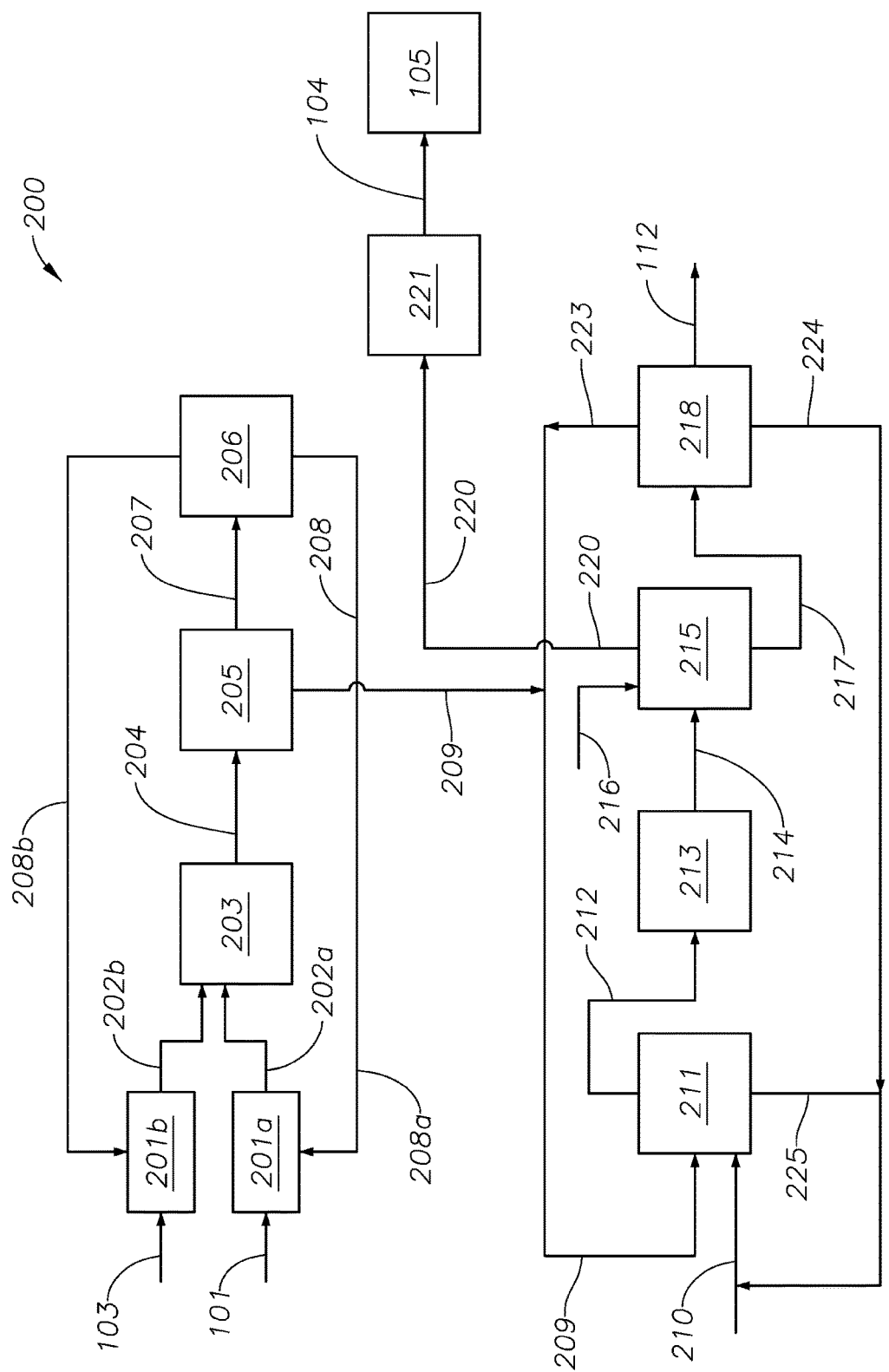
FIG. 2 illustrates an exemplary partial oxidation process 200 according to aspects of the invention.

With continuing reference to FIG. 1, FIG. 2 schematically illustrates a partial oxidation process 200 according to aspects of the invention. Typically, the hydrocarbon feedstock 101 and oxygen-containing gas 103 are separately preheated in preheaters 201a,b to temperatures up to 700° C. before being provided via conduits 202a,b to the furnace 203. Furnace 203 may be of any design suitable for the partial oxidation of the hydrocarbon feedstock. Typically, the furnace 203 includes a mixing zone (not shown), e.g., a diffuser, for mixing the feedstock and the oxygen-containing gas. The furnace will also have a burner block (not shown) that is typically designed to provide a velocity of the oxygen/hydrocarbon mixture that is higher than the flame propagation speed to avoid backing into the mixing zone. The furnace 203 also includes a reaction chamber downstream of the burner block, operable at a temperature of about 1500 to about 2000° C. The reaction chamber may be of any design, typically having a specific volume sufficient to allow the effluent gas mixture 204 (i.e., comprising acetylene and syngas, etc.) to leave the reaction chamber within a few milliseconds, thereby providing a relatively short residence time. After exiting the reaction chamber, the effluent gas mixture 204 is quenched in quench system 205, e.g., a cracked-gas cooling apparatus, to a temperature typically ≤300° C. Quenching may be performed by any suitable method. Water and oil-based quenching methods are described in Ullmann's Encyclopedia of Industrial Chemistry, 5th Edition, Volume A1, pages 97-144.

After quenching, at least a portion of the effluent gas mixture 204 may be provided to soot removal process 206 via one or more conduits 207. Effluent from soot removal process 206 having at least a portion of the soot removed therefrom may be recycled to preheaters 202a,b as may be convenient, e.g., via one or more conduits 208a,b. Quenched effluent exiting quench system 205 is typically provided, e.g., via conduit 209, along with a polar solvent, e.g., N-methyl-pyrrolidone via conduit 210, to a gas-scrubbing unit 211. Gas-scrubbing unit 211 separates the quenched effluent into a polar solvent-enriched stream and a raffinate stream. Polar solvent-enriched stream exits the gas-scrubbing unit 211 via conduit 225 for recycle to the gas-scrubbing unit 211, typically by combination with the contents of conduit 210. The polar solvent-enriched stream may have useful amounts of acetylene retained therein. If desired, such retained acetylene may be removed by any convenient means. The raffinate stream is provided to compressor 213 via conduit 212. Compressed effluent is provided by conduit 214 acetylene absorber unit 215 where the compressed effluent is combined with a polar solvent, e.g., water, provided by conduit 216.

Acetylene absorber unit 215 separates the compressed effluent into a syngas-enriched portion and an acetylene-enriched portion. The syngas-enriched portion separated in acetylene absorber unit 215 is typically provided via conduit 220 to syngas compressor 221 before exiting partial oxidation process 102, e.g., to methanol production process 105 via conduit 104.

The acetylene-enriched portion is typically provided, e.g., via conduit 217, to a carbon-dioxide removal process 218, e.g., a carbon-dioxide stripping unit, for removal of at least a portion of any residual carbon dioxide therein. Carbon dioxide removal process 218 typically separates the acetylene-enriched portion from conduit 217 into a recycle stream, a polar solvent recycle portion, and a purified acetylene stream. Carbon dioxide separated in the carbon dioxide removal process 218 may be recycled e.g., via conduit 223, to gas-scrubbing unit 211 by any convenient method, e.g., combination with quenched effluent in conduit 209. The polar solvent recycle portion exits carbon dioxide removal process 218 via a conduit 224 and is typically recycled to gas-scrubbing unit 211, e.g., by combination with the polar solvent recycle of conduit 225. Acetylene suitable for use in other processes, e.g., the manufacture of acetylene derivatives described herein, may be removed from the partial oxidation process 102 via one or more conduits 112.

Acetylene so-produced may have significantly reduced concentrations of one or more contaminants, e.g., sulfur-containing compounds, nitrogen-containing compounds, and/or calcium-containing compounds. In particular aspects, the concentration of such compounds, individually or in total, may be ≤about 500 pmm, e.g., ≤about 250 pmm, ≤about 125 pmm, ≤about 75 pmm, ≤about 35 pmm, ≤about 20 pmm or ≤about 10 pmm, based on the total weight of the acetylene stream 112.

Some suitable processes are described for example in GB921,305; GB958,046; U.S. Pat. Nos. 2,503,188; 2,679,542; 2,692,902; 2,721,227; 2,765,359; 2,816,942; 2,966,533; 8,080,697; 5,824,834; 5,789,644; 4,725,349; and *Advances in Technology for Preparation of Acetylene via Partial Oxidation of Natural Gas*; Y. Hong; *China Petroleum and Petrochemical Technology*, vol. 10, no. 2, pp. 8-12 (2010). As production capacity of partial oxidation processes can be limited, it may be beneficial to include two or more such partial oxidation processes, typically connected in parallel. Such a configuration not only provides a higher acetylene production capacity, but also may provide a surprising synergy in energy savings relative to a single partial oxidation process operated at substantially the same conditions, particularly in the compression and separation schemes described above. For example, in some processes two or more partial oxidation processes may use ≥5.0% less, e.g., ≥about 7.5 less, ≥about 10.0, ≥about 15.0, or about 20% less energy, based on the total amount of acetylene produced per unit energy, than a single partial oxidation process operated at substantially the same conditions.

Methanol Production Process

Figure 3:
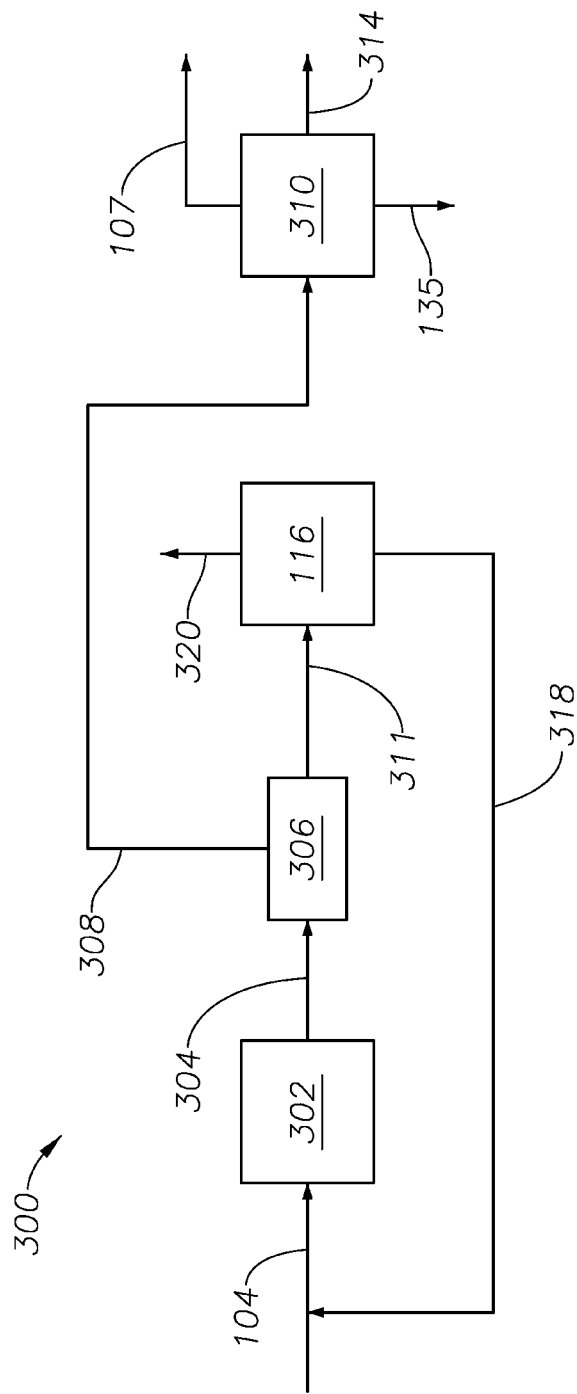
FIG. 3 illustrates an exemplary methanol production process 300 according to aspects of the invention.

Methanol production process 105 may be any process suitable for converting a syngas produced in partial oxidation process 102 to a methanol-containing product. With continuing reference to FIGS. 1 and 2, FIG. 3 schematically illustrates one such process 300. In process 300, compressed syngas from conduit 104 may be provided to one or more reactors 302 and contacted with a methanol synthesis catalyst. Catalysts generally employed for synthesis of methanol are copper based catalysts, especially those containing copper, zinc and a third component which is chromium or the oxide of at least one metal from Groups II to IV of the periodic table, especially aluminum or magnesium. After passage through the catalyst bed, the effluent gases are provided by conduit 304 to heat exchanger 306 to condense the methanol therein. Directly or indirectly thereafter, the mixture of liquid and gases are passed to a separator vessel to separate a methanol-enriched portion and a hydrogen-enriched portion therefrom. Any means may be used to form the methanol-enriched portion and the hydrogen-enriched portion. The methanol-enriched portion is provided by conduit 308 to distillation unit 310. A purified methanol stream exits the distillation unit 310 via conduits 107 and 135, which may be used in subsequent processes described herein, e.g., carbonylation process 108 and/or oxidation unit 136.

The purified methanol of conduit 107 may also have significantly reduced concentrations of one or more contaminants, e.g., sulfur-containing compounds, nitrogen-containing compounds, and/or calcium-containing compounds. In particular aspects, the concentration of such compounds, individually or in total, may be ≤about 500 pmm, e.g., ≤about 250 pmm, ≤about 125 pmm, ≤about 75 pmm, ≤about 35 pmm, ≤about 20 pmm or ≤about 10 pmm, based on the total weight of the methanol stream.

A methanol-depleted stream also exits the distillation unit 310, e.g., via conduit 314, and is typically conducted away from the process. The hydrogen-enriched portion from heat exchanger 306 may be provided, e.g., via conduit 311 to hydrogen/CO separation process 116 for separating hydrogen from light gases, e.g., CO, $C_2$-$C_5$ hydrocarbons, therein. While any means may be used as hydrogen/CO separation process 116, one hydrogen/CO separation process 116 comprises a pressure swing adsorption unit. Such processes are well-known. One such process is described in U.S. Pat. No. 8,231,709, incorporated herein by reference in its entirety. Hydrogen exits hydrogen/CO separation process 116 via, e.g., conduit 318 and may be recycled to process 105, while remaining light gases exit, e.g., via conduit 320 and are typically conducted away from the process.

Some suitable processes are described, for example for use in methanol production process 105 include those described in European Pat. Appl. EP2268774 and U.S. Pat. Nos. 5,472,986; 4,181,675; 6,028,119; 5,032,618; and 5,045,520, each of which is incorporated herein by reference in its entirety.

Carbonylation Process

Figure 4:
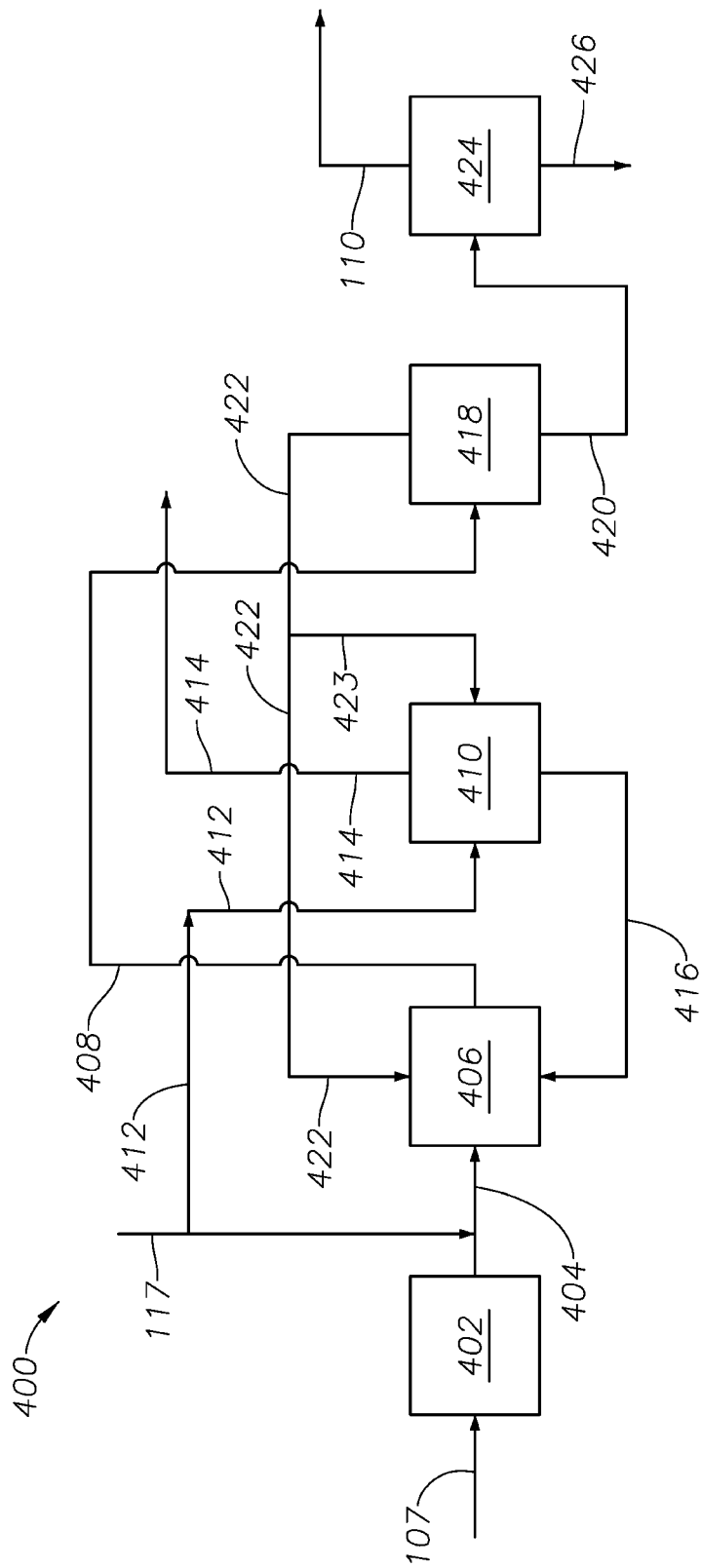
FIG. 4 illustrates an exemplary carbonylation process 400 according to aspects of the invention.

Carbonylation process 108 may be any process suitable for the carbonylation of methanol to produce acetic acid. Methods for the production of acetic acid from methanol are well-known, e.g., the so-called Monsanto and Cativa processes. Any exemplary process 400 is schematically illustrated in FIG. 4. In exemplary process 400, carbon monoxide via conduit 117 is typically provided to compressor 402. Compressed methanol from process 105, e.g., via conduit 107 is combined with the compressed carbon monoxide, e.g., in conduit 404, and is thereafter provided to carbonylation reactor 406. Typical catalysts comprise at least one Group VIII metal-containing catalyst, e.g., a rhodium, iridium, ruthenium, palladium, cobalt or nickel compound. Carbonylation reactor 406 is typically operated at a pressure of from about 0.1 to about 10 MPa, e.g., about 0.35 to about 7.0 MPa, about 0.70 to about 5.0 MPa, about 2.0 to about 3.5 MPa, or about 2.6 to about 3.0 MPa. The temperature of the carbonylation reaction, that is, the temperature in the carbonylation reaction zone of carbonylation reactor 406, ranges between about 50 and about 500° C., e.g., about 75 to about 275° C., about 160 to about 200° C., about 180 to about 190° C.

Effluent from carbonylation reactor typically comprises acetic acid, which exits the reactor via conduit 408. At least a portion of the methanol in conduit 107 may be provided to a scrubbing column 410 via conduit 412. Scrubbing column 410 serves to remove fuel gases, e.g., $C_2$-$C_5$, from the methanol stream. Fuel gases exit the scrubbing column 410 via conduit 414 and are removed from the process. Scrubbed methanol exits the scrubbing unit 410 via conduit 416 and is typically provided to carbonylation reactor 406. Carbonylation effluent in conduit 408 is typically provided to separation unit 418. Any separation unit may be used provided it is capable of purifying the carbonylation effluent, e.g., separating acetic acid in the presence of light gases such as $C_2$-$C_5$ hydrocarbons. Thus, in some embodiments, separation unit 418 is a light ends unit wherein purified carbonylation effluent exits the separation unit 418 via conduit 420 and light ends, e.g., $C_2$-$C_5$ hydrocarbons exit via conduit 422 and may optionally be recycled to carbonylation reactor 406 and/or scrubbing column 410 via, e.g., 423. Purified carbonylation effluent in conduit 420 may be provided to a refining column 424 for further purification, e.g., removal of propionic acid in the case of acetic acid production. Thus, purified acetic acid exits the refining column 424 via conduit 110 for use in subsequent processing as described herein while propionic acid may be removed from the process via conduit 426.

Acetic acid produced by carbonylation process may also have significantly reduced concentrations of one or more contaminants, e.g., sulfur-containing compounds, nitrogen-containing compounds, and/or calcium-containing compounds. In particular aspects, the concentration of such compounds, individually or in total, may be ≤about 500 pmm, e.g., ≤about 250 pmm, ≤about 125 pmm, ≤about 75 pmm, ≤about 35 pmm, ≤about 20 pmm or ≤about 10 pmm, based on the total weight of the acetic acid stream.

Details regarding exemplary processes suitable for use as carbonylation process 108 are described in, e.g., in U.S. Pat. Nos. 3,769,329; 5,155,261; 4,328,125; 5,227,519; 5,237,097; 5,281,359; 5,334,755; 5,360,929; 5,364,963; 5,466,874; 5,744,636; and 6,127,574, each of which is incorporated herein by reference in its entirety.

VAM Production Process

Figure 5:
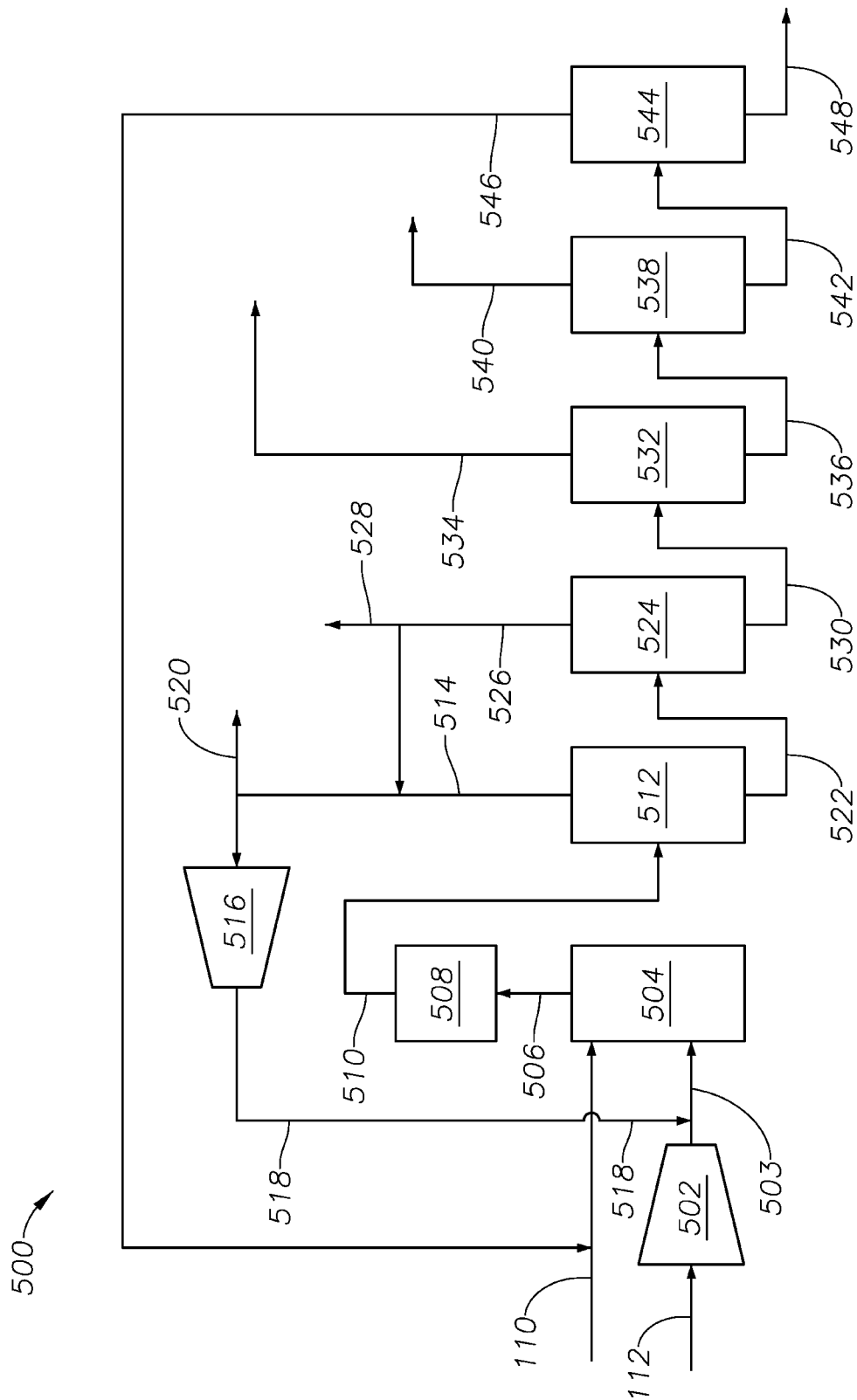
FIG. 5 illustrates an exemplary vinyl acetate monomer (VAM) production process 500 according to aspects of the invention.

Vinyl acetate production process 113 may be any suitable process for converting acetic acid to vinyl acetate monomer. An exemplary process 500 is schematically illustrated in FIG. 5. As illustrated in FIG. 5, acetylene, e.g., from conduit 112 may be compressed in compressor 502 and exits via conduit 503 to be combined with acetic acid of conduit 110 of carbonylation process 108 in vaporizer 504. The combined acetic acid and acetylene from vaporizer 504 are provided via conduit 506 to catalytic reactor 508. Any reactor design or process, e.g., including one or more fluidized or fixed bed reactor processes, may be used as catalytic reactor 508. In an exemplary embodiment, the reactant composition is contacted by a catalyst comprising zinc acetate-impregnated activated carbon and maintained at a temperature from 170 to 220° C. The acetylene and acetic acid vapor can be passed over the catalyst in equimolar quantities or with either reactant in excess, for example with an acetylene to acetic acid molar ratio of 4 to 1.

A reactor effluent stream exits reactor 508 via conduit 510 and is typically passed to vent scrubber 512 where a stream enriched with unreacted acetylene and a crude vinyl acetate stream are formed. The stream enriched with unreacted acetylene exits vent scrubber 512 via conduit 514 for recycle to reactor 508 typically after passing through a compressor 516 prior to being returned to vaporizer 504 via conduit 518. Typically, although not necessarily, a purge line 520 is provided to allow for the release of excess acetylene in conduit 514. The crude vinyl acetate product exits the vent scrubber 512 via conduit 522 and is provided to separation unit 524 for removal of light gases, e.g., $C_2$ to $C_5$ hydrocarbons. Thus, in particular embodiments, separation unit 524 may be a separation column suitable for separating such light gases from vinyl acetate monomer. Light gases exit the separation unit 524 and may be removed from the process via conduit 526 for other uses, e.g., as fuel via conduit 528, or they may be recycled to vaporizer 504, typically after passing through compressor 516 via conduits 514 and 518. The vinyl acetate-containing stream exits separation unit 524 via conduit 530 and is provided to a second separation unit 532 for further separating the vinyl acetate therein from remaining hydrocarbons, including residual acetic acid. Vinyl acetate exits the second separation unit via conduit 534 and is conducted away from the process to a collocated polymerization unit, e.g., a high pressure ethylene/vinyl acetate polymerization process. Further optional separation processes may be utilized. For example, the hydrocarbons separated from the vinyl acetate in second separation unit 532 may be provided to a third separation unit 538 for separating therefrom an intermediate hydrocarbon stream which exits the process via conduit 540, and a heavy fraction which exits the third separation unit 538 via conduit 542. Further optionally, the heavy fraction in conduit 542 may be provided to acetic acid recovery unit 544 for separating residual acetic acid from the heavy hydrocarbons therein. Acetic acid so separated exits acetic acid recovery unit 544 via conduit 546 and is recycled to vaporizer 504, e.g., by combination with acetic acid in conduit 110. Heavy hydrocarbons from acetic acid recovery unit 544 are removed from the process via conduit 548.

Vinyl acetate monomer produced by vinyl acetate monomer process 113 may have significantly reduced concentrations of one or more contaminants, e.g., sulfur-containing compounds, nitrogen-containing compounds, and/or calcium-containing compounds. In particular aspects the concentration of such compounds, individually or in total, may be ≤about 500 pmm, e.g., ≤about 250 pmm, ≤about 125 pmm, ≤about 75 pmm, ≤about 35 pmm, ≤about 20 pmm or ≤about 10 pmm, based on the total weight of the vinyl acetate monomer stream.

Further details regarding exemplary processes and reactors are described in U.S. Pat. Nos. 3,372,187; 4,818,347; 5,066,365; 7,803,965; 8,410,307; and Int'l Pat. Appl. Nos. WO2010066352 and WO2011089070, each of which is incorporated herein by reference in its entirety.

Oxidation Unit

Figure 6:
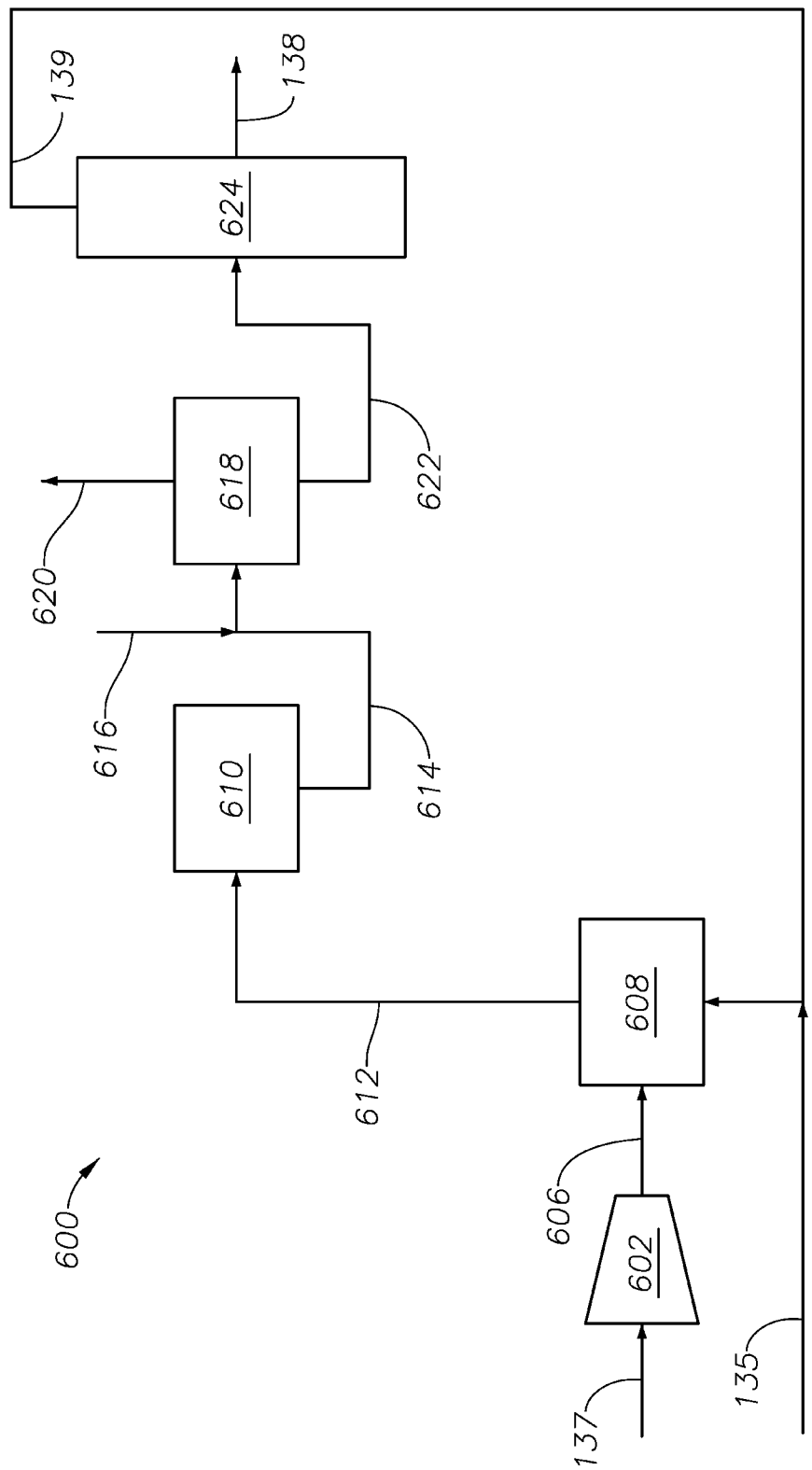
FIG. 6 illustrates an exemplary oxidation unit 600 according to aspects of the invention.

In any embodiment, the integrated process described herein may include an oxidation unit 136 for the production of aldehydes, e.g., formaldehyde from methanol and an oxygen-containing gas. Oxidation unit 136 may be any such suitable process, but typically employs methanol produced from a collocated methanol production process. An exemplary oxidation unit 600 is schematically illustrated in FIG. 6. As illustrated therein, an oxygen-containing gas, e.g., air, is provided to blower 602 via conduit 137. Oxygen containing-gas exits blower 602 via conduit 606 and is combined in evaporator 608 with methanol from conduit 135 of collocated methanol production process 105. The mixture of oxygen-containing gas and methanol exits evaporator 608 and is provided to reactor 610 via conduit 612. Reactor 610 may be of any design suitable for reacting mixture of oxygen-containing gas and methanol. In an exemplary embodiment, reactor 610 is a dehydrogenation reactor operated, batchwise or continuously, at a pressure of about 0.01 to 1 MPa, e.g., 0.05 to 0.2 MPa, or about 0.1 MPa. The temperature of reactor 610 is generally from about 300 to about 950° C., e.g., about 500 to about 900° C., or about 600 to about 850° C.

Typically about 0.01 to 1 kg of methanol per hour and per gram of catalyst used is reacted. In the case of a continuous process, further catalyst has to be introduced continuously or discontinuously. The catalysts used can be, for example, those known from the literature, as are described, for example, in Chem. Eng. Technol. 1994, 17, 34. Suitable catalysts include compositions comprising Li, Na, K, Cs, Mg, Al, In, Ga, Ag, Cu, Zn, Fe, Ni, Co, Mo, Ti, Pt, or their compounds. Also suitable are, for example, S, Se, phosphates of transition metals such as V and Fe, and heteropolyacids such as molybdophosphoric acid. Preferred alloys are those with other alkali metals and/or alkaline earth metals, for example Ba, Sr, Ca, Cs, Rb, K or, particularly preferably, Li and/or magnesium. Other catalyst compositions comprise alloys comprising one or more of the above-enumerated elements and B, Al, Si and/or Sn, e.g., $NaB_2$, $NaSi$, and $NaSn$. In still other embodiments, the catalyst composition comprises one or more sodium carbides, e.g., $Na_2C_2$, $NaC_8$; sodium halides, e.g., NaF; sodium oxides, e.g., $Na_2O$; sodium azide, sodium phosphide, sodium sulfide, sodium polysulfides, and/or NaH.

Effluent exits reactor 610 via conduit 614 and is combined with a polar solvent, e.g., water from conduit 616, and provided to absorber unit 618. Gaseous components exit absorber unit 618 via conduit 620 while a formaldehyde-enriched portion exits the absorber unit 618 via conduit 622. The formaldehyde-enriched portion is thereafter provided to distillation unit 624 for separation of formaldehyde from other components therein, particularly methanol. Thus, a purified formaldehyde stream exits distillation unit 624 via conduit 140 for use in other processes while other components, primarily methanol, exit via conduit 139 and are removed from the process or recycled to the reactor 610, typically via evaporator 608.

Formaldehyde produced by oxidation unit 136 may have significantly reduced concentrations of one or more contaminants, e.g., sulfur-containing compounds, nitrogen-containing compounds, and/or calcium-containing compounds. In particular aspects, the concentration of such compounds, individually or in total, may be ≤about 500 pmm, e.g., ≤about 250 pmm, ≤about 125 pmm, ≤about 75 pmm, ≤about 35 pmm, ≤about 20 pmm or ≤about 10 pmm, based on the total weight of the oxidation product stream, e.g., formaldehyde, stream.

Further details regarding exemplary processes and reactors may be found in U.S. Pat. Nos. 6,362,305; 4,967,014; 6,379,507; 2,467,223; 3,459,807; and 3,978,136, each of which is incorporated herein by reference it its entirety.

Diol Unit

Figure 7:
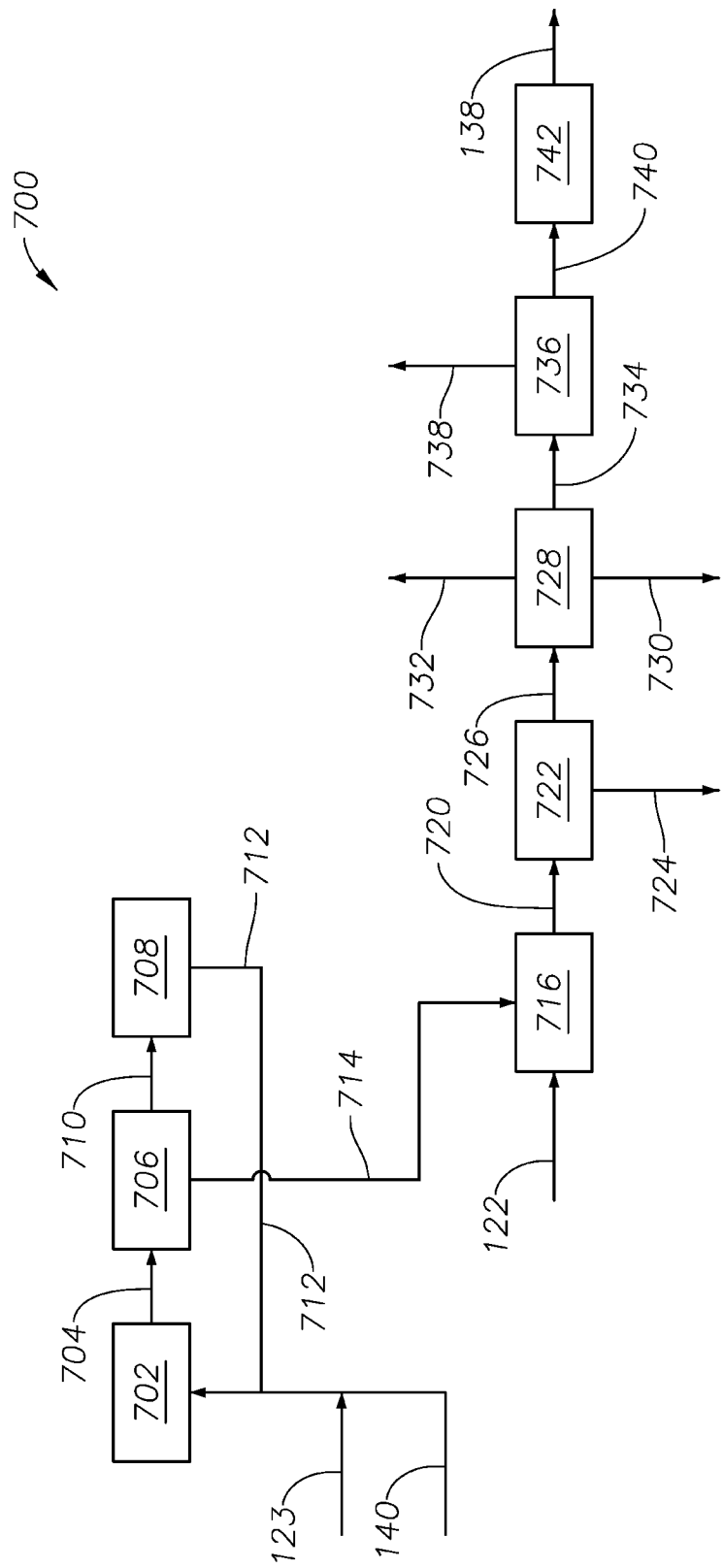
FIG. 7 illustrates an exemplary 1,4-butanediol production process 700 according to aspects of the invention.

In any embodiment, the integrated process described herein may include a 1,4-butanediol production unit 121. Diol unit 121 may be any suitable process for converting formaldehyde and acetylene to 1,4-Butanediol production (BDO). An exemplary process 700 is schematically illustrated in FIG. 7. As illustrated in FIG. 7, formaldehyde, e.g., from conduit 140 of oxidation unit 136, is combined with acetylene, e.g., from conduit 112 of partial oxidation process 102, and provided to reactor 702. Reactor 702 may be any reactor configuration suitable for converting the mixture of formaldehyde and acetylene to 1,4-butanediol. For example, the reaction of acetylene and formaldehyde can be effected in one or more reactors connected in parallel or series. The catalysts may be used in suspension, in a fluidized bed and/or a fixed bed. The reaction of formaldehyde and acetylene by means of a fixed bed can be conducted in any convenient mode, e.g., in trickle mode or liquid-phase mode. The molar ratio of formaldehyde:acetylene in reactor 702 is typically about 2:1. The presence of free acetylene surprisingly prevents the premature aging or destruction of the catalyst. Preference is therefore given to either using a molar ratio of acetylene to formaldehyde of at least 0.5:1, e.g., about 0.0501:1 to about 0.55:1, as early as at the start of the reaction or to metering in additional acetylene at various points in the reaction zone during the reaction.

Reactor 702 may be operated at a temperature typically from about 30 to about 130° C., e.g., 50 to about 100° C., or about 65 to about 90° C. Residence times of from about 0.5 to about 200 hr., e.g., about 1 to about 100 hr., about 5 to about 50 hr., are typically suitable. Catalysts used for the reaction of acetylene with formaldehyde are described, for example, in German Pat. Nos. DE-A 22 09 520; DE-A 22 09 521; DE-A 23 57 752; DE-A 23 57 751; DE-A 26 02 418; and DE-A 197 53 458, each of which is incorporated herein by reference in its entirety. Exemplary such catalyst compositions comprise copper and optionally bismuth, e.g., as described in DE-A 26 02 418 wherein the catalyst composition comprises bismuth and copper on a silicon dioxide support.

Intermediate product comprising 1,4-butynediol (BYO) leaves reactor 702 and is provided to first and second separation units 706 and 708 via conduits 704 and 710, respectively. First separation unit 706 directs a BYO-depleted stream, typically including methanol and residual formaldehyde, via conduit 710 to second separation unit 708. Separation unit 708 reduces the methanol content of the BYO-depleted stream. A formaldehyde-enriched stream exits second separation unit 708 via conduit 712 and is recycled to reactor 702 via, e.g., conduit 626. A BYO-enriched stream exits first separation unit 706 via conduit 714 and is provided to hydrogenation unit 716 along with a hydrogen-source, e.g., compressed hydrogen via conduit 122 for conversion to BDO. Processes for the hydrogenation of BYO to BDO are well-known. Exemplary processes and conditions are described in U.S. Pat. Nos. 3,119,879; 5,714,644; 4,111,849; and 7,288,686, each of which is incorporated herein by reference in its entirety.

The crude product from hydrogenation unit 716 is provided via conduit 720 to a separation unit 722. Any separation unit may be used as separation unit 722. Typically, separation unit 722 is designed to separate at least a portion of heavy ends from the crude BDO-containing stream in conduit 720. Thus, a heavy ends-enriched portion exits separation unit 722 and is removed from the process for disposal or use, e.g., as fuel via conduit 724. A BDO-enriched stream exits separation unit via conduit 726 and is provided to water removal unit 728. A water-enriched stream exits water removal unit 728 via conduit 730. A light end fraction, e.g., $C_2$-$C_4$ hydrocarbons, may also be removed in the water removal unit 728, e.g., via conduit 732, for use in other processes. A purified BDO-enriched stream exits water removal unit 728 via conduit 734 and is provided to separation unit 736. Separation unit 736 may be any separation unit suitable for reducing the concentration of any remaining undesired components in the purified BDO-enriched stream. In one embodiment, separation unit 736 is configured to separate the purified BDO-enriched stream from conduit 734 into butanol-enriched stream that exits the separation unit 736 via conduit 738 and is conducted away from the process. Separation unit 736 also provides a BDO-containing butanol-depleted stream which exits the unit 736 via conduit 740 and is optionally provided to a BDO recovery column 742 for further purification, from which exits a purified BDO- stream via conduit 138.

1,4-butanediol produced by diol unit 121 may have significantly reduced concentrations of one or more contaminants, e.g., sulfur-containing compounds, nitrogen-containing compounds, and/or calcium-containing compounds. In particular aspects, the concentration of such compounds, individually or in total, may be ≤about 500 pmm, e.g., ≤about 250 pmm, ≤about 125 pmm, ≤about 75 pmm, ≤about 35 pmm, ≤about 20 pmm or ≤about 10 pmm, based on the total weight of the 1,4-butanediol stream.

Hydrogen Chloride Unit and VCM Unit

Figure 8:
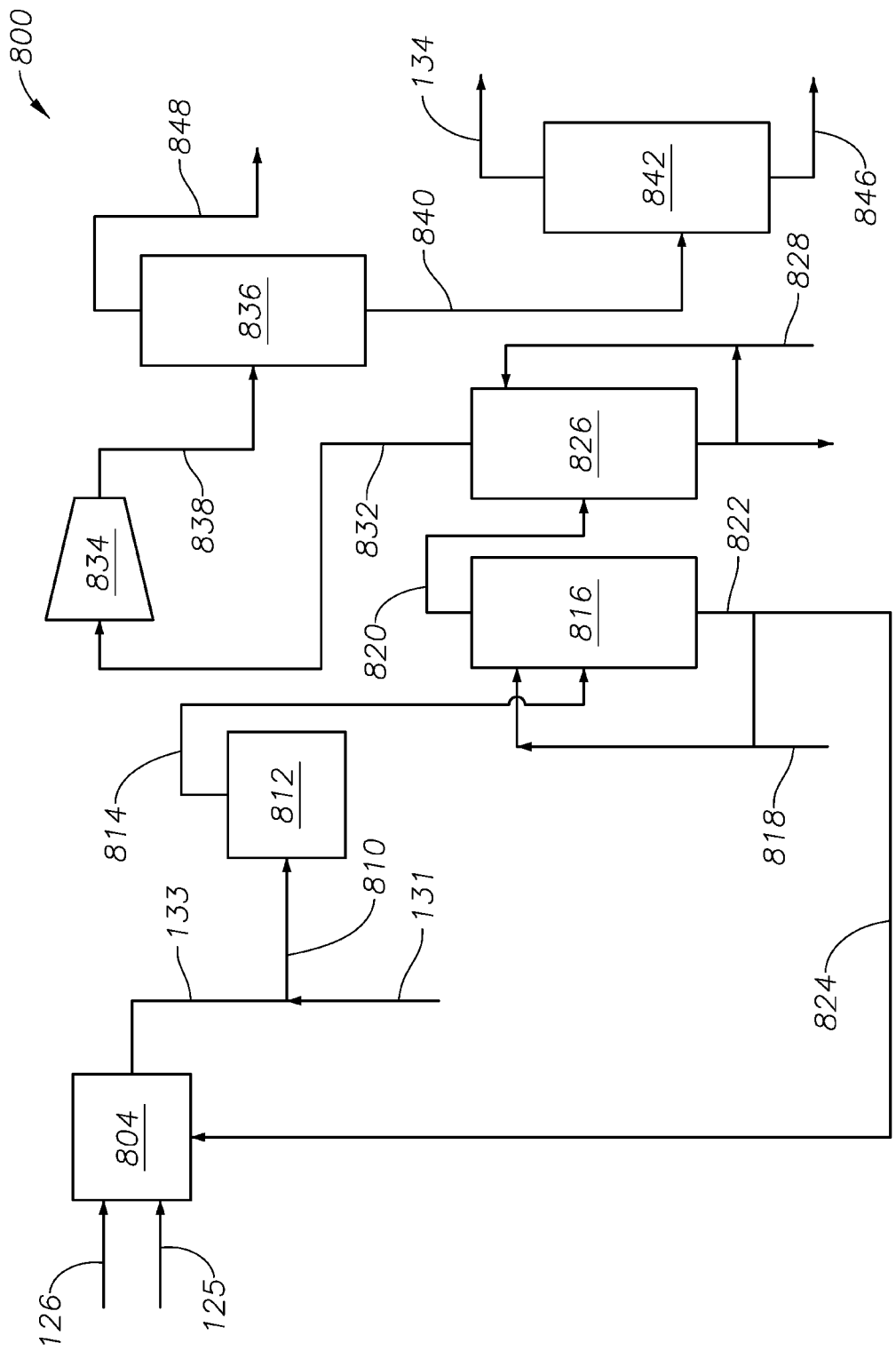
FIG. 8 illustrates an exemplary vinyl chloride monomer (VCM) production process 800 according to aspects of the invention.

In any embodiment, the integrated process described herein may include a vinyl chloride monomer (VCM) unit 132 and/or a hydrogen chloride unit 124. For convenience these processes are described together and they may be any suitable process for providing hydrogen chloride or converting hydrogen chloride and acetylene to vinyl chloride monomer. Exemplary processes 800 are schematically illustrated in FIG. 8. As illustrated in FIG. 8, a chloride agent, e.g., chlorine gas, may be provided via conduit 126 along with hydrogen gas, e.g., via conduit 125, to reactor 804. Reactor 804 may be any reactor suitable for the reaction of hydrogen and chlorine. Such reactors are well-known in the art and need not be further described here. Hydrogen chloride so produced may be provided via conduit 133 and combined with acetylene, e.g., via conduit 131, and provided via conduit 810 along to reactor 812. Reactor designs and process conditions for the gas-phase reaction of hydrogen chloride and acetylene are well-known. Exemplary such processes are described in U.S. Pat. Nos. 2,705,732; 2,830,102; 3,125,608; and 3,723,550, each of which is incorporated herein by reference in its entirety.

After reaction in reactor 812, a crude product stream exits the reactor 812 via conduit 814. The crude product stream may be purified by any suitable means. In an exemplary process, the crude product stream in conduct 814 is provided to a water scrubber 816 along with water via conduit 818. A scrubbed VCM-containing effluent exits water scrubber 816 via conduit 820. An aqueous wash, typically including an appreciable amount of HCl therein, exits the water scrubber via conduit 822 and may be recycled to the scrubbing unit, e.g., via combination with the contents of conduit 818, or to reactor 804 via conduit 824. Typically, the water-scrubbed VCM-containing effluent is thereafter provided to a caustic scrubbing unit 826 wherein a caustic agent, e.g., aqueous solution of NaOH, etc., is provided via conduit 828 to the caustic scrubbing unit 822. Spent caustic wash exits caustic scrubbing unit 826 via conduit 830. Caustic-scrubbed VCM-containing effluent exits the caustic scrubbing unit via conduit 832 and is provided to compressor 834 prior to entering VCM Stripping unit 836 via conduit 838. Stripped VCM-containing effluent exits VCM stripping unit 836 via conduit 840 and enters finishing column 842. Purified vinyl chloride monomer exits finishing column 842 via conduit 134 and may be used in any convenient process, e.g., a vinyl chloride polymerization process. Heavy ends exit the finishing column 842 via conduit 846 and are conducted away from the process. Likewise, heavy ends obtained from stripping unit 836 may by carried away from the process via conduit 848 for further treatment or use.

Vinyl chloride monomer produced by VCM unit 132 may have significantly reduced concentrations of one or more contaminants, e.g., sulfur-containing compounds, nitrogen-containing compounds, and/or calcium-containing compounds. In particular aspects, the concentration of such compounds, individually or in total, may be ≤about 500 pmm, e.g., ≤about 250 pmm, ≤about 125 pmm, ≤about 75 pmm, ≤about 35 pmm, ≤about 20 pmm or ≤about 10 pmm, based on the total weight of the vinyl chloride monomer stream.

ADDITIONAL EMBODIMENTS

Embodiment 1

An integrated process for the production of one or more acetylene derivatives, the process comprising: a) partially oxidizing a hydrocarbon feedstock comprising ≥10 wt. % of one or more $C_1$-$C_4$ alkanes to produce a partial oxidation mixture comprising $H_2$, CO, and acetylene, b) providing at least a portion of the $H_2$ and CO of the partial oxidation mixture to a collocated methanol production process to produce a methanol-containing effluent; c) providing at least a portion of the methanol-containing effluent to a collocated carbonylation process to produce an acetic acid-containing effluent; and d) providing at least a portion of the acetylene of the partial oxidation mixture and at least a portion of the acetic acid-containing effluent to one or more collocated acetylene-derivative processes following: i) a vinyl acetate monomer production process; ii) an oxidation unit for the production of formaldehyde from the methanol-containing effluent; iii) a vinyl chloride monomer production process, and/or iv) a 1,4-butanediol production process.

Embodiment 2

The process of Embodiment 1, wherein the one or more collocated acetylene-derivative processes comprise a vinyl acetate monomer production process.

Embodiment 3

The process of Embodiment 1 or 2, wherein the one or more collocated acetylene-derivative processes comprise an oxidation unit for the production of formaldehyde from the methanol-containing effluent.

Embodiment 4

The process of any of Embodiments 1 to 3, wherein the one or more collocated acetylene-derivative processes comprise a vinyl chloride monomer production process.

Embodiment 5

The process of any of Embodiments 1 to 4, wherein the one or more collocated acetylene-derivative processes comprise a 1,4-butanediol production process.

Embodiment 6

The process of any of Embodiments 1 to 5, wherein the one or more collocated acetylene-derivative processes comprise a) a vinyl acetate monomer production process and b) an oxidation unit for the production of formaldehyde from the methanol-containing effluent.

Embodiment 7

The process of any of Embodiments 1 to 6, wherein the one or more collocated acetylene-derivative processes comprise a) a vinyl acetate monomer production process and b) a vinyl chloride monomer production process.

Embodiment 8

The process of any of Embodiments 1 to 7, wherein the one or more collocated acetylene-derivative processes comprise a) a vinyl acetate monomer production process and b) a 1,4-butanediol production process.

Embodiment 9

The process of any of Embodiments 1 to 8, wherein the one or more collocated acetylene-derivative processes comprise a) an oxidation unit for the production of formaldehyde from the methanol-containing effluent and b) a vinyl chloride monomer production process.

Embodiment 10

The process of any of Embodiments 1 to 9, wherein the one or more collocated acetylene-derivative processes comprise a) an oxidation unit for the production of formaldehyde from the methanol-containing effluent and b) a 1,4-butanediol production process.

Embodiment 11

The process of any of Embodiments 1 to 10, wherein the one or more collocated acetylene-derivative processes comprise a) a vinyl chloride monomer production process and b) a 1,4-butanediol production process.

Embodiment 12

The process of any of Embodiments 1 to 11, wherein the one or more collocated acetylene-derivative processes comprise a) a vinyl acetate monomer production process; b) an oxidation unit for the production of formaldehyde from the methanol-containing effluent; and c) a vinyl chloride monomer production process.

Embodiment 13

The process of any of Embodiments 1 to 12, wherein the one or more collocated acetylene-derivative processes comprise a) a vinyl acetate monomer production process; b) an oxidation unit for the production of formaldehyde from the methanol-containing effluent; and c) a 1,4-butanediol production process.

Embodiment 14

The process of any of Embodiments 1 to 13, wherein the one or more collocated acetylene-derivative processes comprise a) a vinyl acetate monomer production process; b) a vinyl chloride monomer production process, and c) a 1,4-butanediol production process.

Embodiment 15

The process of any of Embodiments 1 to 14, wherein the one or more collocated acetylene-derivative processes comprise a) an oxidation unit for the production of formaldehyde from the methanol-containing effluent; b) a vinyl chloride monomer production process, and c) a 1,4-butanediol production process.

Embodiment 16

The process of any of Embodiments 1 to 15, wherein the one or more collocated acetylene-derivative processes comprise a) a vinyl acetate monomer production process; b) an oxidation unit for the production of formaldehyde from the methanol-containing effluent; c) a vinyl chloride monomer production process, and d) a 1,4-butanediol production process.

Embodiment 17

The process of any of Embodiments 1 to 16, wherein the one or more collocated acetylene-derivative processes comprise a 1,4-butanediol production process and the formaldehyde provided thereto comprises ≤about 7.5 wt %, e.g., ≤about 5.0 wt %, ≤about 2.5 wt %, ≤about 1.0 wt %, or ≤about 0.5 wt % methanol.

Embodiment 18

The process of any of Embodiments 1 to 17, wherein the at least a portion of the acetylene provided to the one or more collocated acetylene-derivative processes comprises ≤about 7.5 wt %, e.g., ≤about 5.0 wt %, ≤about 2.5 wt %, ≤about 1.0 wt %, or ≤about 0.5 wt % acetone.

Embodiment 19

The process of any of Embodiments 1 to 18, wherein the partial oxidation process comprises two or more partial oxidation reactors having a per unit energy requirement ≥5.0% less, e.g., ≥about 7.5 less, ≥about 10.0, ≥about 15.0, or about 20% than that of a single partial oxidation process, based on the total amount of acetylene produced per unit energy.

Embodiment 20

The process of any of Embodiments 1 to 19, characterized by a carbon footprint ≤about 95% of a comparable process.

Without wishing to be held to any particular theory, it is believed that BDO made according to a process where acetylene and/or formaldehyde are provided from one or more collocated processes is substantially free of undesirable components, e.g., stabilizers, additives, and/or impurities introduced conventional processes where one or more of the acetylene and/or formaldehyde must be transported, e.g., via ground transport or ship, to the BDO manufacturing facility. In particular embodiments, the BDO so produced may have ≥about 75 wt % less, e.g., ≥about 50 wt % less, ≥about 25 wt % less, ≥about 20 wt % less, or ≥about 10 wt % less of such stabilizer or impurity, based on the amount of such stabilizer or impurity derived from acetylene and/or formaldehyde in a BDO made by a process where either one or more of the acetylene and/or formaldehyde is provided by a process that is not integrated with the diol unit 121. In particular embodiments, formaldehyde produced by oxidation unit and thereafter provided to any downstream process, e.g., the 1,4-butanediol production process, comprises ≤about 7.5 wt %, e.g., ≤about 5.0 wt %, ≤about 2.5 wt %, ≤about 1.0 wt %, or ≤about 0.5 wt % methanol. Additionally or alternatively, in some embodiments, acetylene produced in partial oxidation process 102 and provided to any downstream process comprises ≤about 7.5 wt %, e.g., ≤about 5.0 wt %, ≤about 2.5 wt %, ≤about 1.0 wt %, ≤about 0.5 wt % acetone, ≤about 0.1 wt % acetone, ≤about 0.01 wt % acetone. It is also believed that the integrated nature of the process described herein provides reduced contamination of one or more downstream processes by sulfur-containing, nitrogen-containing and/or calcium-containing compounds that act as catalyst poisons. Thus, one or more process steps of the integrated process described herein may benefit from a need for fewer reactant stream sacrificial beds and/or other reactant purification steps with respect to comparable processes that are not integrated. Additionally or alternatively, the integrated process described herein may have a reduced environmental impact as evidenced by a reduced carbon footprint. For example, the carbon footprint of one or more integrated process described herein may be ≤about 95%, e.g., ≤about 92.5%, ≤about 90.0%, ≤about 87.5%, ≤about 85.0%, of a comparable un-integrated process. Methods for determining the carbon impact of such processes are well known.

All documents described herein are incorporated by reference herein for purposes of all jurisdictions where such practice is allowed, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. An integrated process for the production of one or more acetylene derivatives, the process comprising:
   a) partially oxidizing a hydrocarbon feedstock comprising 10.0 wt. % or more of one or more $C_1$-$C_4$ alkanes to produce a partial oxidation mixture comprising $H_2$, CO, and acetylene,
   b) providing at least a portion of the $H_2$ and CO of the partial oxidation mixture to a collocated methanol production process to produce a methanol-containing effluent;
   c) providing at least a portion of the methanol-containing effluent to a collocated carbonylation process to produce an acetic acid-containing effluent; and
   d) providing at least a portion of the acetylene of the partial oxidation mixture and at least a portion of the acetic acid-containing effluent to one or more collocated acetylene-derivative processes following:
      i) a vinyl acetate monomer production process;
      ii) an oxidation unit for the production of formaldehyde from the methanol-containing effluent;
      iii) a vinyl chloride monomer production process, and/or
      iv) a 1,4-butanediol production process.

2. The process of claim 1, wherein the one or more collocated acetylene-derivative processes comprises a vinyl acetate monomer production process.

3. The process of claim 1, wherein the one or more collocated acetylene-derivative processes comprises an oxidation unit for the production of formaldehyde from the methanol-containing effluent.

4. The process of claim 1, wherein the one or more collocated acetylene-derivative processes comprises a vinyl chloride monomer production process.

5. The process of claim 1, wherein the one or more collocated acetylene-derivative processes comprises a 1,4-butanediol production process.

6. The process of claim 1, wherein the one or more collocated acetylene-derivative processes comprise a) a vinyl acetate monomer production process and b) an oxidation unit for the production of formaldehyde from the methanol-containing effluent.

7. The process of claim 1, wherein the one or more collocated acetylene-derivative processes comprise a) a vinyl acetate monomer production process and b) a vinyl chloride monomer production process.

8. The process of claim 1, wherein the one or more collocated acetylene-derivative processes comprise a) a vinyl acetate monomer production process and b) a 1,4-butanediol production process.

9. The process of claim 1, wherein the one or more collocated acetylene-derivative processes comprise a) an oxidation unit for the production of formaldehyde from the methanol-containing effluent and b) a vinyl chloride monomer production process.

10. The process of claim 1, wherein the one or more collocated acetylene-derivative processes comprise a) an oxidation unit for the production of formaldehyde from the methanol-containing effluent and b) a 1,4-butanediol production process.

11. The process of claim 1, wherein the one or more collocated acetylene-derivative processes comprise a) a vinyl chloride monomer production process and b) a 1,4-butanediol production process.

12. The process of claim 1, wherein the one or more collocated acetylene-derivative processes comprise a) a vinyl acetate monomer production process; b) an oxidation unit for the production of formaldehyde from the methanol-containing effluent; and c) a vinyl chloride monomer production process.

13. The process of claim 1, wherein the one or more collocated acetylene-derivative processes comprise a) a vinyl acetate monomer production process; b) an oxidation unit for the production of formaldehyde from the methanol-containing effluent; and c) a 1,4-butanediol production process.

14. The process of claim 1, wherein the one or more collocated acetylene-derivative processes comprise a) a vinyl acetate monomer production process; b) a vinyl chloride monomer production process, and c) a 1,4-butanediol production process.

15. The process of claim 1, wherein the one or more collocated acetylene-derivative processes comprise a) an oxidation unit for the production of formaldehyde from the methanol-containing effluent; b) a vinyl chloride monomer production process, and c) a 1,4-butanediol production process.

16. The process of claim 1, wherein the one or more collocated acetylene-derivative processes comprise a) a vinyl acetate monomer production process; b) an oxidation unit for the production of formaldehyde from the methanol-containing effluent; c) a vinyl chloride monomer production process, and d) a 1,4-butanediol production process.

17. The process of claim 1, wherein the one or more collocated acetylene-derivative processes comprise a 1,4-butanediol production process and the formaldehyde provided thereto comprises ≤about 7.5 wt % methanol.

18. The process of claim 1, wherein the at least a portion of the acetylene provided to the one or more collocated acetylene-derivative processes comprise ≤about 7.5 wt % acetone.

19. The method of claim 1, wherein the partial oxidation process comprises two or more partial oxidation reactors having a per unit energy requirement ≥5.0% less than that of a single partial oxidation process, based on the total amount of acetylene produced per unit energy.

20. The process of claim 1, characterized by a carbon footprint ≤about 95% of a comparable process.

* * * * *